United States Patent
Bhambure et al.

(10) Patent No.: US 11,697,672 B2
(45) Date of Patent: Jul. 11, 2023

(54) PROCESS FOR THE PURIFICATION OF RECOMBINANT ANTIBODY FRAGMENTS

(71) Applicant: COUNCIL OF SCIENTIFIC AND INDUSTRIAL RESEARCH, New Delhi (IN)

(72) Inventors: Rahul Sharad Bhambure, Pune (IN); Kayanat Mahammadtaki Gani, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 826 days.

(21) Appl. No.: 16/496,895

(22) PCT Filed: Mar. 23, 2018

(86) PCT No.: PCT/IN2018/050164
§ 371 (c)(1),
(2) Date: Sep. 23, 2019

(87) PCT Pub. No.: WO2018/173075
PCT Pub. Date: Sep. 27, 2018

(65) Prior Publication Data
US 2020/0095277 A1    Mar. 26, 2020

(30) Foreign Application Priority Data
Mar. 24, 2017 (IN) .............................. 201711010410

(51) Int. Cl.
*C07K 1/16* (2006.01)
*C07K 16/22* (2006.01)
(Continued)

(52) U.S. Cl.
CPC .................. *C07K 1/36* (2013.01); *C07K 1/16* (2013.01); *C07K 16/22* (2013.01); *C07K 16/24* (2013.01); *C07K 1/14* (2013.01); *C07K 1/165* (2013.01); *C07K 1/34* (2013.01); *C07K 16/065* (2013.01); *C07K 2317/55* (2013.01); *C07K 2319/02* (2013.01)

(58) Field of Classification Search
CPC . C07K 1/16; C07K 1/165; C07K 1/36; C07K 16/00; C07K 16/22; C07K 2317/55
See application file for complete search history.

(56) References Cited

U.S. PATENT DOCUMENTS

2013/0338344 A1* 12/2013 Ramasubramanyan ..................... C12P 21/00 530/416
2016/0289314 A1   10/2016 Shandilya et al.
2017/0058019 A1*  3/2017 Felföldi .................. B01J 41/20

FOREIGN PATENT DOCUMENTS

WO   WO 2014/178078 A2   11/2014
WO   WO 2017/029620 A1   2/2017

OTHER PUBLICATIONS

Maria et al. (2015, J. Chromatog. 1393:57-64).*
(Continued)

*Primary Examiner* — Jeffrey E. Russel
(74) *Attorney, Agent, or Firm* — Blank Rome LLP

(57) ABSTRACT

The present invention relates to a purification process of recombinant antibody fragments from inclusion bodies expressed in microbial cells. More particularly, the present invention relates to a process for purification of recombinant humanized (rHu) antibody fragment, Ranibizumab from inclusion bodies expressed in microbial cells.

7 Claims, 9 Drawing Sheets

(51) Int. Cl.
*C07K 1/36* (2006.01)
*C07K 16/24* (2006.01)
*C07K 1/14* (2006.01)
*C07K 1/34* (2006.01)
*C07K 16/06* (2006.01)

(56) References Cited

OTHER PUBLICATIONS

Maria et al. Purification process of recombinant monoclonal antibodies with mixed mode chromatography. Journal of Chromatography A. May 1, 2015, vol. 1393, pp. 57-64. (Year: 2015).*
Scanlan et al. Challenges and Strategies for the Downstream Purification and Formulation of Fab Antibody Fragments. Biopharm International. Jan. 1, 2014, vol. 27, No. 1, pp. 42-44. (Year: 2014).*
"J.T. Baker® BAKERBOND® PolyCSX™ multimode strong cation exchange chromatography resin," avantorsciences.com/ Technical Note, Mar. 2021.
GE Healthcare, "Capto MMC," Instructions 11-0035-05 AA, Multimodal media, 2005.
General Electric Company, "Capto™ adhere," Instructions 28906405 AD, Multimodal Chromatography, Nov. 2017.
J.T. Baker, BAKERBOND™ XWP 500 Poly PEI-35, Product No. 7585, Lot No. K12085, Release Date Apr. 13, 2011.
J.T. Baker, BAKERBOND™ XWP 500 PolyCSX-35, Product No. 7587, Lot No. L14088, Release Date Apr. 19, 2012.
GE Healthcare, Safety Data Sheet, Catalogue No. 17-5444-10, Validation Date Mar. 1, 2015.
GE Healthcare, Material Safety Data Sheet, Catalogue No. 17-3716-99, Validation Date Aug. 27, 2013.
Pall Corporation, Safety Data Sheet—MEP, HEA, PPA and CMM HyperCel™, 2016.

* cited by examiner

PROCESS FOR THE PURIFICATION OF RECOMBINANT ANTIBODY FRAGMENTS

RELATED APPLICATIONS

This application is a national phase application of PCT/IN2018/050164, filed Mar. 23, 2018, which claims priority to Indian Application No. 201711010410, filed Mar. 24, 2017.

FIELD OF THE INVENTION

The present invention relates to a process for the purification of recombinant antibody fragments from inclusion bodies expressed in microbial cells. More particularly, the present invention relates to a process for the purification of recombinant humanized (rHu) antibody fragment, Ranibizumab from inclusion bodies expressed in microbial cells.

BACKGROUND OF THE INVENTION

The recent trend in biopharmaceuticals research and development is more focused on development of antibody fragments. Although a large number of biosimilar therapeutic proteins are in development than ever before, critical challenges in the biosimilar product development are, higher downstream processing costs, non-selective clearance of process and product related impurities, proteolytic degradation of the product etc. Antibody fragments offer certain advantages over the full size monoclonal antibody (mAb) therapeutics such as improved and deep tumor penetration, binding to specific epitopes which are not accessible to full size mAb etc. Fabs account for the majority of antibody fragment candidates that have entered clinical development, and three have been approved by US FDA. Advancement in upstream processes such as high titer clones and continuous bio-manufacturing has shifted the focus of biopharmaceutical industries towards improving the overall downstream process economics. The downstream processing constitutes approximately 60-70% of the overall manufacturing cost for monoclonal antibody therapeutics. The capture, intermediate and polishing steps of downstream processing involves extensive use of various chromatographic operations. Ranibizumab is a (Vascular Endothelial Growth Factor-A) VEGF-A antagonist that binds to and inhibits the biological functioning of active forms of human VEGF-A. Excessive up-regulation of VEGF-A renders it to play a critical role in the growth of new blood vessels leading to angiogenesis and hyper-permeability of the vessels. Permeability of blood vessels may result in macular edema and choroidal neovascularization, thereby causing the wet type of age-related macular degeneration (AMD). Therefore, to control and treat the diseased condition of hyper permeability of blood vessels, it is essential to inhibit VEGF-A by means of the VEGF-A antagonist. Ranibizumab is commercially available in a medicinal formulation as Lucentis® and is administered via intravitreal injection. It is specifically designed and manufactured for intraocular use. Ranibizumab is a recombinant humanized IgG1 kappa isotype monoclonal antibody fragment designed for intraocular use in the treatment of age-related macular degeneration (ARMD).

The molecular weight of Ranibizumab is approximately 48.37 kDa, i.e. 23.43 kDa and 24.95 kDa for the light and heavy chain respectively. The humanized monoclonal antibody fragment is expressed in E. coli cells by recombinant DNA technology and is targeted against the human vascular endothelial growth factor A (VEGF-A). Ranibizumab is a 214-residue light chain linked by a disulfide bond at its C-terminus to the 231-residue N-terminal segment of the heavy chain. Prior art literature provides evidences focusing on the expression of antibody fragments and its purification. However, recombinant humanized (rHu) Ranibizumab produced using E. coli cells forms inclusion bodies in the form of insoluble protein aggregates.

US20160289314 discloses cloning, expression and purification method for the preparation of Ranibizumab. The purification process merely involves reduction, oxidation and in-vitro refolding of the solubilized inclusion bodies followed by step wise process of ultrafiltration and diafiltration-I, anion exchange chromatography, cation exchange chromatography, ultrafiltration and diafiltration-II, and filtration. The multiple purification steps in this process lead to low throughput operation thereby making the process cumbersome.

Therefore, there is a dire need to provide a convenient downstream procedure to obtain purified antibody fragment. In light of the drawbacks posed by the downstream purification procedures of the prior art disclosures, the present inventors have attempted to provide a process for purification of antibody fragments. The resultant purified antibody fragment obtained by the present invention satisfies and meets the purity and activity standards of the innovator product.

OBJECTS OF THE INVENTION

The main object of the present invention is thus to provide a process for the purification of antibody fragments.

Another object of the present invention is to provide a process for the purification of recombinant Ranibizumab by integrating the multimodal chromatographic purification steps with rHu Ranibizumab downstream processing.

Yet another object of the present invention is to provide a process which results in almost two-fold improvement in productivity over existing manufacturing processes.

Still another object of the present invention is to provide a process wherein the developed purification platform is applicable to both in-vitro refolded and soluble expressed antibody fragments.

SUMMARY OF THE INVENTION

The present invention provides a process for the purification of recombinant antibody fragments.

In an embodiment, the present invention relates to a process for the purification of recombinant human Ranibizumab from recombinant host cells, the said process comprising; obtaining rHu Ranibizumab from a recombinant host cell in the form of inclusion bodies; solubilizing inclusion bodies using solubilization buffer to obtain solubilized rHu Ranibizumab; refolding solubilized rHu Ranibizumab using refolding buffer to obtain refolded rHu Ranibizumab; concentrating refolded rHu Ranibizumab by ultra-filtration to obtain concentrated rHu Ranibizumab; subjecting concentrated rHu Ranibizumab to sequential multimodal chromatography purification steps to remove product related impurities, host cell proteins and host cell nucleic acids followed by diafiltration and ultrafiltration to obtain purified rHu Ranibizumab.

In another embodiment, the present invention provides multimodal chromatography purification stages comprising the steps of;
(i) subjecting concentrated refolded rHu Ranibizumab to multimodal chromatography feeding concentrated, refolded rHu Ranibizumab having pH ranging from 4.0 to 10.0 onto a multimodal chromatography resin to capture rHu Ranibizumab and eliminate impurities with a buffer comprising 20 mM to 50 mM Tris HCl and 0 mM to 150 mM NaCl or 20 mM to 50 mM acetate and 0 mM to 150 mM NaCl with pH ranging from 4.0 to 10.0;

(ii) eluting rHu Ranibizumab in the presence of an elution buffer comprising 20 mM to 50 mM Tris HCl and 0 mM to 1000 mM sodium chloride or 20 mM to 50 mM acetate and 0 mM to 1000 mM NaCl with pH ranging from 4.0 to 10.0 into an elution pool, wherein purified Ranibizumab has less than 5% of unfolded or misfolded forms of Ranibizumab and less than 2% of aggregated form of Ranibizumab;

(iii) feeding rHu Ranibizumab obtained from step (ii) having pH ranging from 4.5 to 6.5 onto a multimodal chromatography resin to capture rHu Ranibizumab and further eliminate impurities with a buffer comprising 20 mM to 50 mM acetate and 0 mM to 150 mM NaCl having pH ranging from 4.0 to 6.5;

(iv) eluting rHu Ranibizumab in the presence of an elution buffer comprising 20 mM to 50 mM acetate and 0 mM to 1000 mM NaCl having pH ranging from 4.0 to 6.5;

wherein purified rHu Ranibizumab has less than 0.1% of unfolded or misfolded forms of rHu Ranibizumab and less than 0.3% of aggregated form of rHu Ranibizumab.

In still another embodiment, the present invention provides a process of multimodal chromatography, wherein the sequence of the multimodal chromatography phases I and II are interchangeable.

In yet another embodiment, the present invention provides recombinant humanized Ranibizumab obtained by the downstream process for purification of Ranibizumab.

This summary is provided to introduce concepts related to methods of purifying recombinant human antibody fragment (rHu Ranibizumab). This summary is not intended to identify essential features of the claimed subject matter nor is it intended for use in determining or limiting the scope of the claimed subject matter.

BRIEF DESCRIPTION OF THE ACCOMPANYING DRAWINGS

Figure 4:
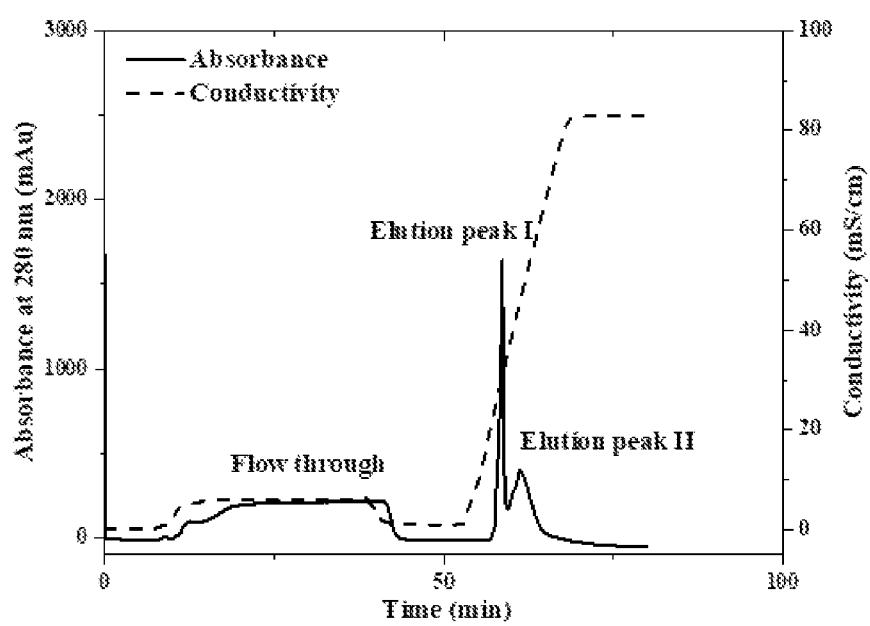
Figure 5:
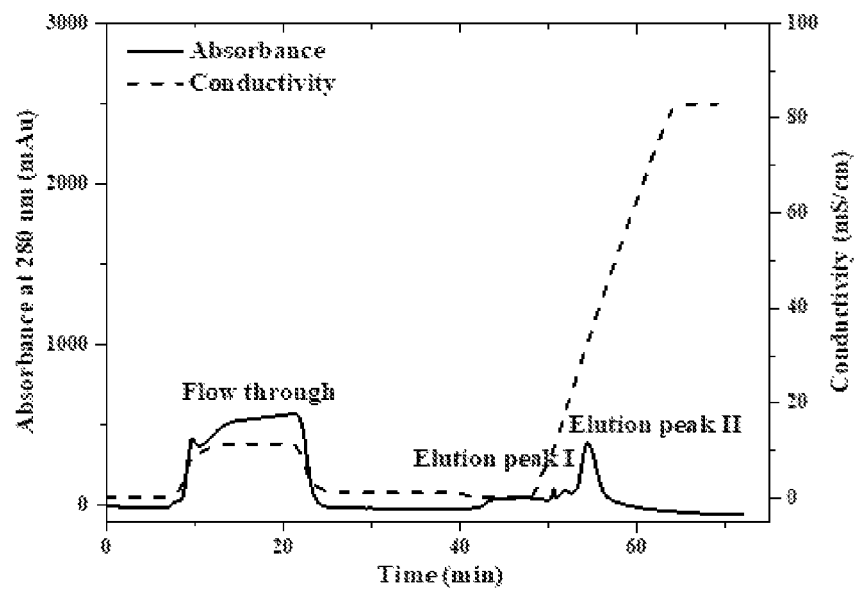
Figure 6:
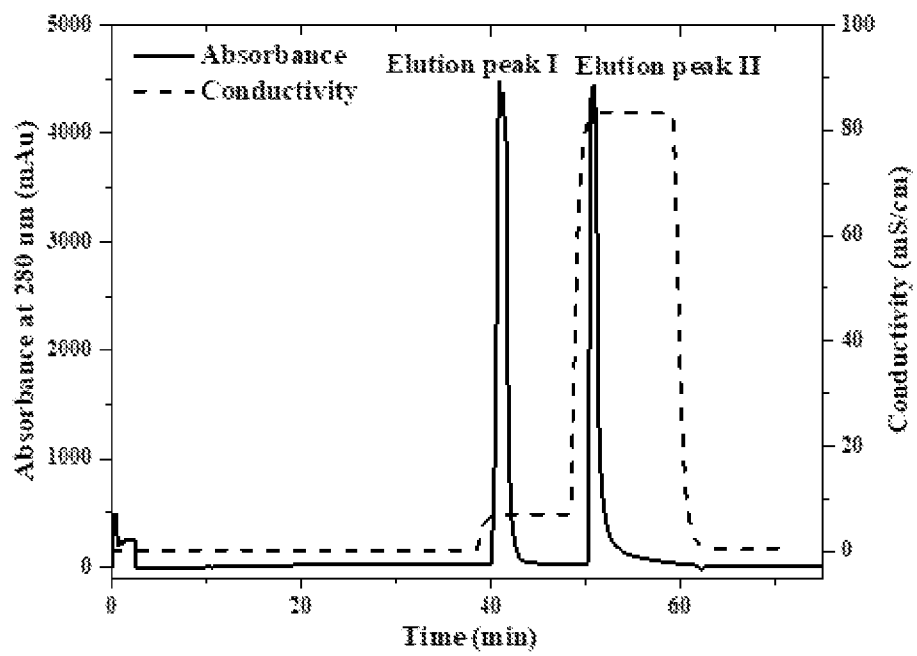
Figure 7:
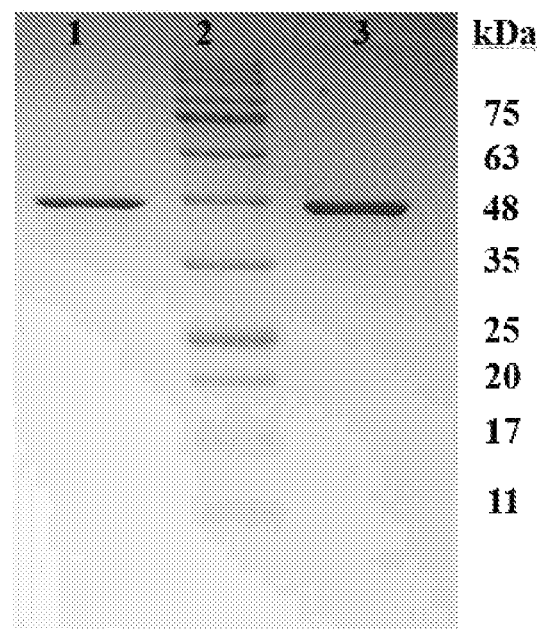
Figure 8:
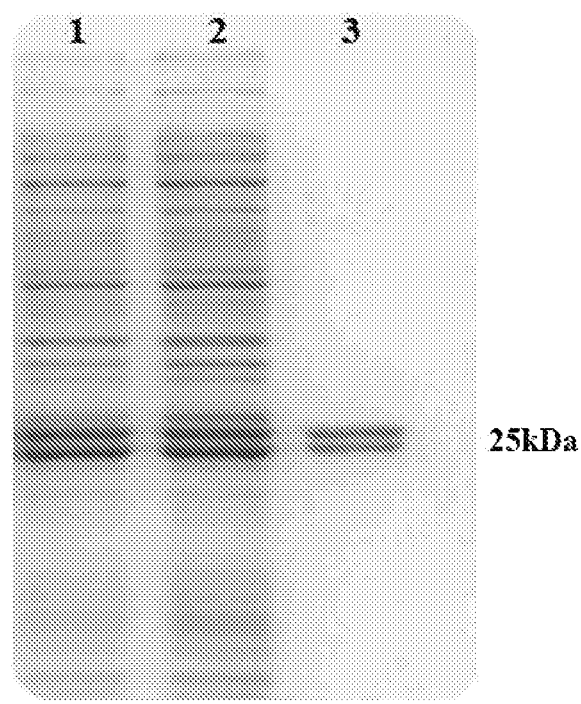
Figure 9:
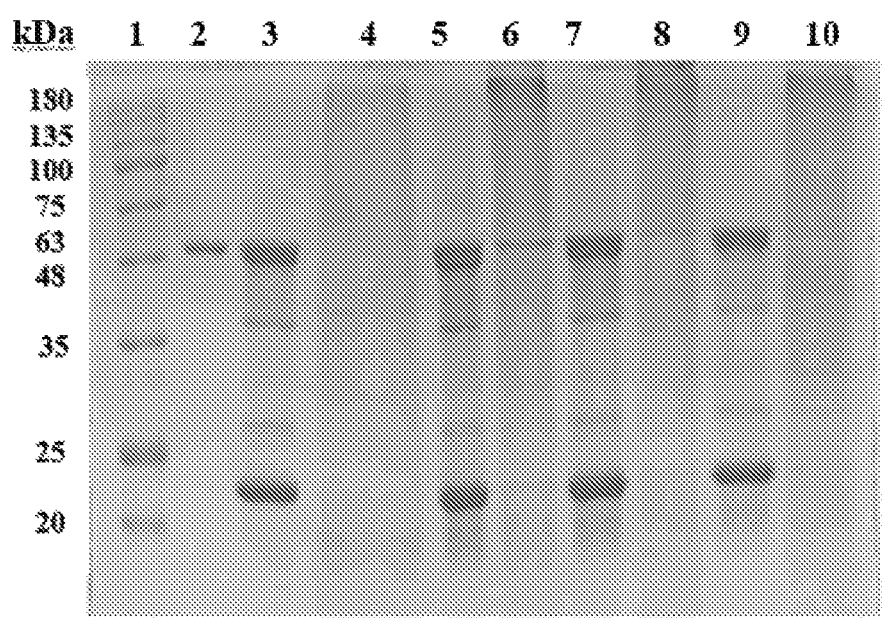
Figure 10:
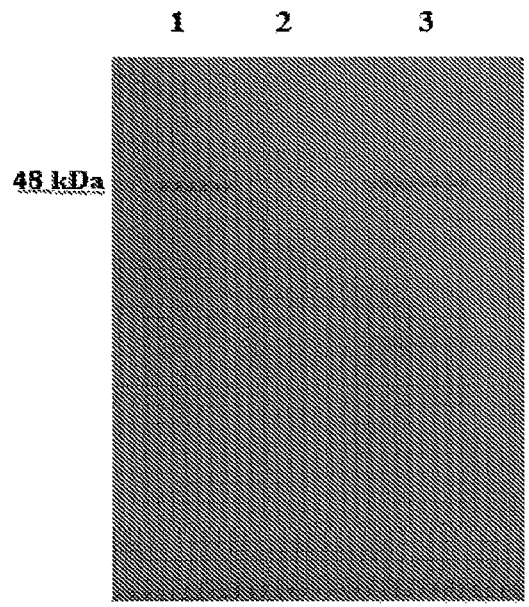

FIG. 4 depicts chromatogram for flow through mode multimodal chromatography I (Feed material conductivity: 6.0 mS/cm, Equilibration buffer: 20.0 mM Tris pH 9.0, Refolded rHu Ranibizumab eluted using 5.0 CV salt gradient) Flow through: Purified rHu Ranibizumab (29.69% purity); Elution peak I: Process related impurities (Host cell proteins and nucleic acids) including rHu Ranibizumab, Elution peak II: misfolded and unfolded Ranibizumab and process related impurities;

FIG. 5 depicts chromatogram for flow through mode multimodal chromatography I (Feed material conductivity: 12.0 mS/cm, Equilibration buffer: 20.0 mM Tris pH 9.0, Refolded rHu Ranibizumab eluted using 5.0 CV salt gradient), Flow through: Purified rHu Ranibizumab (33.12%); Elution peak I: Process related impurities (Host cell proteins and nucleic acids), Elution peak II: misfolded and unfolded Ranibizumab and process related impurities;

FIG. 6 depicts chromatogram for multimodal chromatography I (Equilibration buffer: 20.0 mM Tris pH 9.0, refolded rHu Ranibizumab was eluted by step gradient, first step was 12.5% of elution buffer and second step was 100% elution buffer comprising 20 mM Tris pH 9.0 with 1.0 M NaCl); Elution peak I: Purified rHu Ranibizumab (38.25% purity), Elution peak II: Product (misfolded and unfolded Ranibizumab) and process related impurities;

FIG. 7 depicts a non-reducing SDS-PAGE for characterization of low and high molecular weight impurities associated with refolded rHu Ranibizumab, Lane 1: Refolded purified rHu Ranibizumab using multimodal chromatography of present invention, Lane 2: Protein molecular weight marker, and Lane 3: Standard innovator Ranibizumab;

FIG. 8 depicts reducing SDS-PAGE. Lane 1: Refolded purified rHu Ranibizumab, Lane 2: Protein molecular weight marker, and Lane 3: Standard innovator Ranibizumab;

FIG. 9 depicts Non-reducing SDS-PAGE of elution peaks form Multimodal chromatography I: 1: Protein molecular weight marker. 2: Standard innovator rHu Ranibizumab. 3: Elution peak 1 (With 38.25% purity of refolded rHu Ranibizumab at 48 kDa having low molecular weight impurities), 4: Elution peak 2 (Showing all other process related impurities), (Condition of Multimodal chromatography I: equilibration buffer pH 9.0, refolded rHu Ranibizumab was eluted at 5 CV salt gradient), 5: Elution peak 1, 6: Elution peak 2, (condition Equilibration buffer pH 10.0, refolded rHu Ranibizumab was eluted at 5 CV salt gradient); 7: Elution peak 1, 8: Elution peak 2, (condition Equilibration buffer pH 10.0, refolded rHu Ranibizumab was eluted at 7.5 CV salt gradient); 9: Elution peak 1, 10: Elution peak 2, (condition Equilibration buffer pH 10.0, refolded rHu Ranibizumab was eluted at 10 CV salt gradient);

FIG. 10 depicts Non-reducing SDS-PAGE of purified soluble expressed rHu Ranibizumab: 1: Standard innovator rHu Ranibizumab, 3: Purified rHu Ranibizumab of the present invention.

Figure 11A:
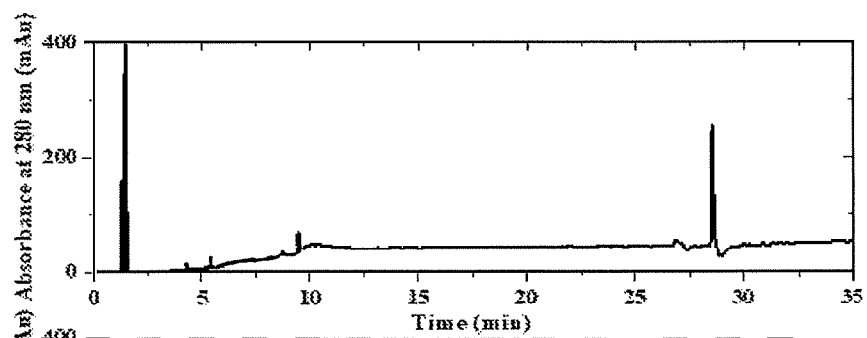
Figure 11B:
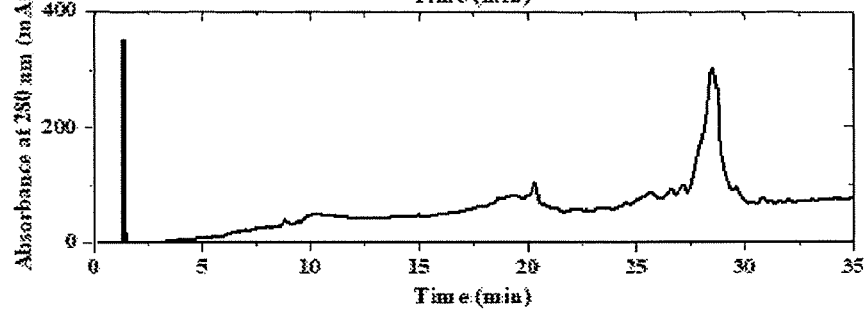
Figure 12A:
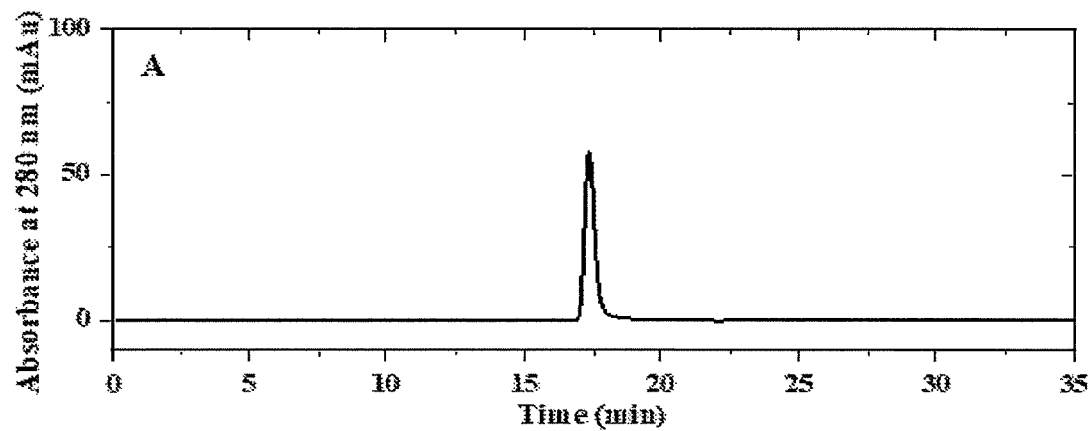
Figure 12B:
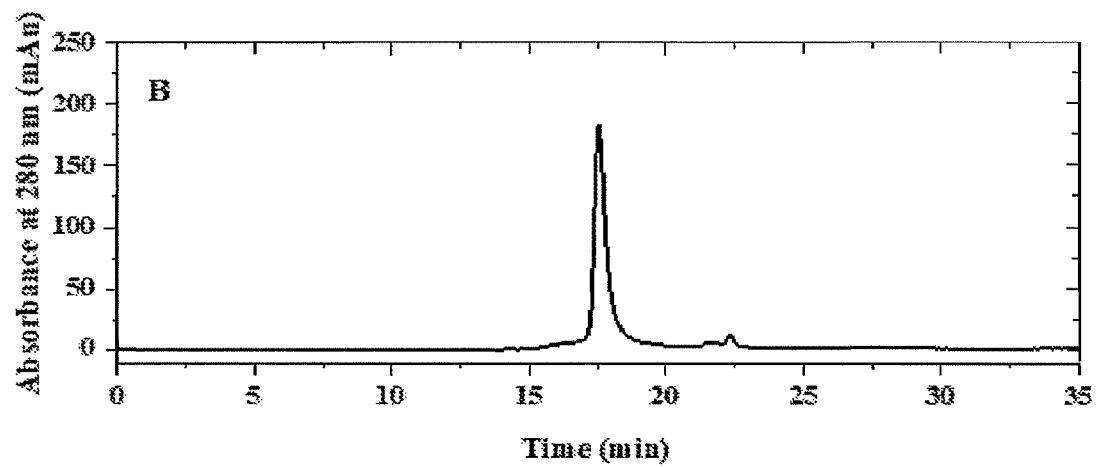
Figure 13A:
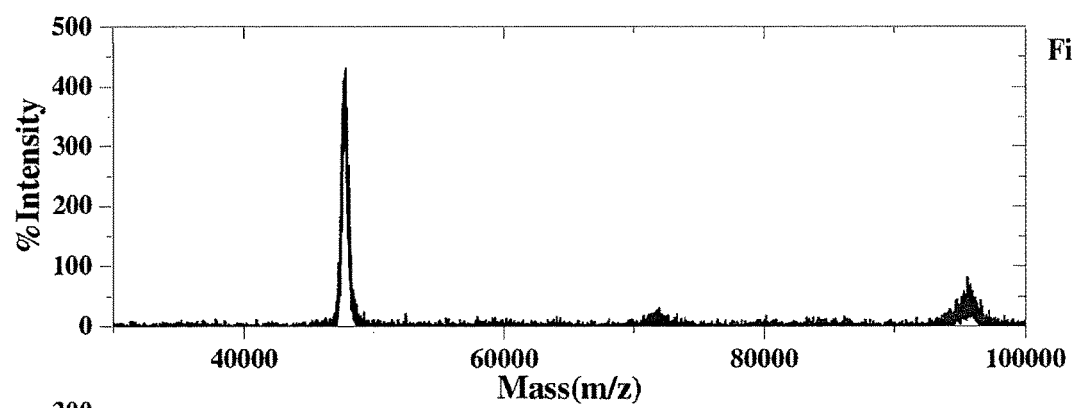
Figure 13B:
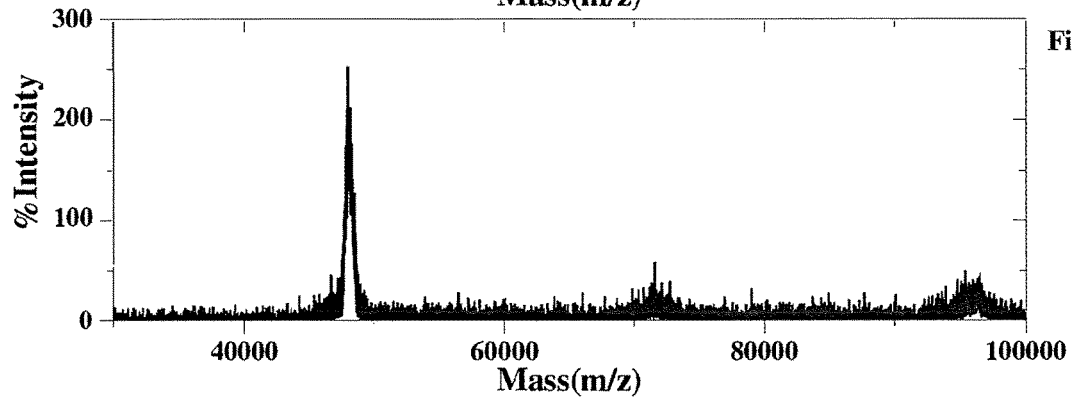

FIGS. 11A-B depict reversed phase HPLC chromatograms for purity analysis of purified rHu Ranibizumab. (FIG. 11A: Standard innovator rHu Ranibizumab. FIG. 11B: Purified rHu Ranibizumab);

FIGS. 12A-B depict size exclusion chromatograms of purified rHu Ranibizumab. (FIG. 12A: Standard innovator rHu Ranibizumab. FIG. 12B: Purified rHu Ranibizumab);

FIGS. 13A-B depict intact mass analysis by MALDI-TOF. (FIG. 13A: Standard innovator rHu Ranibizumab, FIG. 13B: Purified rHu Ranibizumab).

FIG. 13 depicts intact mass analysis by MALDI-TOF. A: Standard innovator rHu Ranibizumab, B: Purified rHu Ranibizumab.

DETAILED DESCRIPTION OF THE INVENTION

The invention will now be described in detail in connection with certain preferred and optional embodiments, so that various aspects thereof may be more fully understood and appreciated.

Definitions

For convenience, before further description of the present invention, certain terms employed in the specification, examples and appended claims are collected here.

The term "inclusion bodies" refers to insoluble, aggregates of target recombinant protein. Inclusion bodies of the target protein contain combination of misfolded and partially folded protein. Protein refolding is the process by which a protein acquires its native three dimensional structure, a conformation that is biologically functional.

The term "reducing agent" refers to a substance which causes reduction of disulfide linkages of the protein and keep both intra and inter molecular disulfide bonds chemically disrupted.

The term "chaotropic agent" refers to a substance which is capable of altering the protein conformation making it more water soluble. Examples of such chaotropic agents include ethanol, butanol, urea, guanidium hydrochloride, thiourea, magnesium chloride, lithium perchlorate etc.

The term "host cell protein" refers to all the proteins which are expressed by the host cell apart from the target protein during the course of fermentation or cell culture process.

The term 'multi-modal chromatography' used herein refers to a chromatography technique wherein the ligand interacts with the protein through multiple types of interactions including ionic interaction, hydrophobic interaction or hydrogen bonding.

The present invention provides a process for purification of recombinant monoclonal antibody fragments from a recombinant host cell, the said process comprising;
  (i) solubilizing inclusion bodies containing an antibody fragment obtained from recombinant host cells using a solubilization buffer to obtain solubilized antibody fragments;
  (ii) refolding the solubilized antibody fragment using a refolding buffer to obtain refolded antibody fragments;
  (iii) concentrating the refolded antibody fragments by ultra-filtration to obtain concentrated antibody fragments; and
  (iv) subjecting concentrated antibody fragments to sequential multimodal chromatography purification to remove product related impurities, namely host cell proteins, and host cell nucleic acids followed by diafiltration and ultrafiltration to obtain purified rHu antibody fragments.

Recombinant Ranibizumab is obtained by the expression of the said protein in preferably equal proportion of heavy and light chain concentration in the recombinant host cells. The recombinant host cell used in the present invention is that of *E. coli*. The *E. coli* host strain used in the present invention is *E. coli* BL21 (DE3). The said strain was obtained from Merck Millipore.

The present invention provides solubilizing inclusion bodies containing equal or unequal proportion of light and heavy chains of recombinant humanized (rHu) Ranibizumab in the presence of a solubilization buffer to obtain a solubilized mixture of light and heavy chains of rHu Ranibizumab. The rHu inclusion bodies extracted from the recombinant host cell were solubilized using solubilization buffer comprising a combination of a chaotropic detergent, reducing agent and a denaturing agent.

Chaotropic reagent includes urea and guanidium hydrochloride salts. The pH of the solubilization buffer was maintained in the range of 7 to 10. Reduction of the solubilized inclusion bodies was achieved using a combination of the reducing agents which includes dithiothreitol, beta mercaptoethanol for 30 minutes to 2 hours.

The chaotropic detergent, reducing agent and denaturing agent is selected from those that are conventionally used in the art.

The process for solubilization comprises initially solubilizing inclusion bodies obtained from a recombinant host cell containing Ranibizumab protein in 15 ml solubilization buffer. The solubilization buffer contains 0.1 M Tris pH 9.0, 2 mM EDTA and 6M guanidine hydrochloride as a denaturant for 30 min followed by reduction in the presence of 5 mM DTT for 1 hr. The soluble and reduced inclusion body solution was kept for oxidation by adding 10 mM oxidized glutathione.

In another embodiment, in-vitro refolding of the solubilized rHu Ranibizumab is obtained in the presence of a refolding buffer. The refolding buffer comprises a protein folding agent, a polyol and a surfactant, wherein the pH is maintained between 8.0 to 10.0.

'In-vitro protein refolding' referred herein relates to a process of converting the misfolded Ranibizumab into the correctly folded form. Ranibizumab refolding was achieved using 75-fold dilution at a temperature ranging from 5° C. to 20° C. in refolding buffer containing 0.1 M Tris pH 9.0, 0.6 M Arginine, 5% Sorbitol and 2 mM EDTA.

The refolded Ranibizumab protein is further concentrated by ultra-filtration using 5 kDa ultrafiltration Ultrasette™ Lab Tangential Flow Filtration device and then buffer exchanged into 20 mM Tris pH 9.0. The buffer exchanged samples were then used as an input for multimodal chromatography.

In the most preferred embodiment, the present invention provides a process for purifying antibody fragments of recombinant humanized (rHu) Ranibizumab from a recombinant host cell comprising;
  (a) solubilizing inclusion bodies containing light and heavy chains of rHu Ranibizumab from a recombinant host cell to obtain solubilized rHu Ranibizumab;
  (b) refolding solubilized rHu Ranibizumab to obtain refolded rHu Ranibizumab;
  (c) concentrating refolded rHu Ranibizumab by ultrafiltration to obtain concentrated, refolded Ranibizumab;
  (d) subjecting the concentrated refolded rHu Ranibizumab to multimodal chromatography, the said chromatography process comprising;
    (i) feeding concentrated, refolded rHu Ranibizumab of step (c) having pH ranging from 4.0 to 10.0 onto a multimodal chromatography resin to capture rHu Ranibizumab and eliminate impurities with a buffer comprising 20 mM to 50 mM Tris HCl and 0 mM to 150 mM NaCl or 20 mM to 50 mM acetate and 0 mM to 150 mM NaCl with pH ranging from 4.0 to 10.0;
    (ii) eluting rHu Ranibizumab in the presence of an elution buffer comprising 20 mM to 50 mM Tris HCl and 0 mM to 1000 mM sodium chloride or 20 mM to 50 mM acetate and 0 mM to 1000 mM NaCl with pH ranging from 4.0 to 10.0 into an elution pool, wherein purified Ranibizumab has less than 5% of unfolded or misfolded forms of Ranibizumab and less than 2% of aggregated form of Ranibizumab;
    (iii) feeding rHu Ranibizumab from step (ii) having pH ranging from 4.5 to 6.5 onto a multimodal chromatography resin to capture rHu Ranibizumab and further eliminate impurities with a buffer comprising 20 mM to 50 mM acetate and 0 mM to 150 mM NaCl having pH ranging from 4.0 to 6.5;

(iv) eluting rHu Ranibizumab in the presence of an elution buffer comprising 20 mM to 50 mM acetate and 0 mM to 1000 mM NaCl having pH ranging from 4.0 to 6.5;

wherein purified rHu Ranibizumab has less than 0.1% of unfolded or misfolded forms of rHu Ranibizumab and less than 0.3% of aggregated form of rHu Ranibizumab.

The process stages involved in multimodal chromatography purification in steps (i) and (ii) of the aforementioned process are referred to as multimodal chromatography phase I and process stages involved in multimodal chromatography purification in steps (iii) and (iv) of the aforementioned process are referred to as multimodal chromatography phase II. Multimodal chromatography phases I and II are performed in a sequential manner or may be optionally interchanged in sequence to remove various process and product related impurities associated with rHu Ranibizumab.

The Multimodal chromatography phases I (process steps (i) and (ii)) and II (process steps (iii) and (iv)) involve two steps each for purification of rHu Ranibizumab.

In an embodiment, the present invention provides multimodal chromatography phase I comprising bind elute mode of multimodal chromatography and flow through mode of multimodal chromatography.

In another embodiment, the present invention provides multimodal chromatography phase II comprising bind elute mode of multimodal chromatography and flow through mode of multimodal chromatography.

Multimodal Chromatography Phase I:

The multimodal chromatography mode employed in phase I is selected from bind elute chromatography mode or flow through mode. The multimodal chromatography resin I is selected from the group consisting of HEA Hypercel™ a high porosity cross-linked cellulose having hexylamine ligands), PPA Hypercel™ a high porosity cross-linked cellulose having phenylpropylamine ligands), and BAKERBOND™ XWP 500 Poly PEI-35 (a hydrophilic polymer with polyethyleneimine bonded thereon) or Capto™ adhere (a cross-linked agarose matrix having covalently bonded N-benzyl-N-methyl ethanol amine ligands) resin.

The present invention provides multimodal chromatography phase I involving bind elute mode of chromatography comprises;

(i) binding concentrated, refolded rHu Ranibizumab onto a multimodal chromatography resin I to capture rHu Ranibizumab and eliminate impurities with a buffer comprising 20 mM to 50 mM Tris HCl and 0 mM to 150 mM NaCl having pH ranging from 8.0 to 10.0;

(ii) eluting rHu Ranibizumab in presence of an elution buffer comprising 20 mM to 50 mM Tris HCl and 0 mM to 1000 mM sodium chloride with pH ranging from 8.0 to 10.0 into an elution pool.

The first stage of multimodal chromatography phase I involving bind-elute chromatography comprises binding refolded rHu Ranibizumab and eluting purified refolded rHu Ranibizumab.

In multimodal chromatography resin I, change in sample input pH from 8.0 to 10.0, and eluting in different salt gradient from 5 CV to 10 CV play an important role in the removal of impurity and optimization of purification process.

In bind and elute mode of multimodal chromatography phase I, change in equilibration buffer pH from 8.0 to 10.0, change in the charge distribution and three dimensional conformation of protein. By combination of ionic interaction, hydrophobic interaction and elution in different salt gradient, it was observed that in equilibration buffer pH 9.0 and 5 CV salt gradient, a recovery of 67.56% with product purity of 38.79% was obtained.

In one embodiment, the present invention provides a binding buffer used for binding rHu Ranibizumab to the multimodal chromatography resin I comprising;

(i) 20 mM to 50 mM Tris-HCl, and (ii) 0 mM to 150 mM sodium chloride, with pH in the range of 8.0 to 10.0.

In another embodiment, the present invention provides an elution buffer used for eluting rHu Ranibizumab from multimodal chromatography resin I into an elution pool comprising;

(i) 20 mM to 50 mM Tris-HCl, and (ii) 0 mM to 1000 mM sodium chloride with pH in the range of 8.0 to 10.0.

The present invention provides multimodal chromatography phase I involving flow through mode of chromatography comprising;

(i) feeding concentrated, refolded rHu Ranibizumab with input conductivity ranging from 6.0 mS/cm to 12 mS/cm onto a multimodal chromatography resin I to capture rHu Ranibizumab and eliminate impurities with a buffer comprising 20 mM to 50 mM acetate and 0 mM to 150 mM NaCl having pH ranging from 4.0 to 6.5; and (ii) eluting impurities in presence of an elution buffer comprising 20 mM to 50 mM acetate and 0 mM to 1000 mM sodium chloride with pH ranging from 4.0 to 6.5 into an elution pool.

In the flow through mode of multimodal chromatography phase I, changing the input conductivity of the refolded concentration fraction of recombinant Ranibizumab results in a change in the binding affinity of refolded rHu Ranibizumab and impurities. At 12 mS/cm of sample input conductivity, impurity was bound with resin and refolded rHu Ranibizumab was eluted out in flow through. It was observed that under such conditions a recovery of 76.98% with product purity of 33.12% was obtained.

Multimodal Chromatography Phase II:

rHu Ranibizumab obtained from the elute of multimodal chromatography phase I is adjusted to pH ranging from 4.5 to 6.5, feeding onto a multimodal chromatography resin II to capture rHu Ranibizumab and further eliminate impurities with a buffer comprising 20 mM to 50 mM acetate and 0 mM to 150 mM NaCl having pH ranging from 4.0 to 6.5.

The present invention provides multimodal chromatography phase II performed employing the bind elute chromatography, the said process comprising;

(i) feeding rHu Ranibizumab obtained from the elution pool of multi modal chromatography phase I having pH ranging from 4.5 to 6.5 with input conductivity ranging from 6.0 mS/cm to 12 mS/cm onto a multimodal chromatography resin II to capture rHu Ranibizumab and further eliminate impurities with a buffer comprising 20 mM to 50 mM acetate and 0 mM to 150 mM NaCl having pH ranging from 4.0 to 6.5;

(ii) eluting rHu Ranibizumab in the presence of an elution buffer comprising 20 mM to 50 mM acetate and 0 mM to 1000 mM NaCl having pH ranging from 4.0 to 6.5.

The present invention provides multimodal chromatography phase II performed employing flow through mode of multimodal chromatography, the said process comprising;

(i) feeding rHu Ranibizumab obtained from the elution pool of multi modal chromatography phase I having pH ranging from 8.0 to 10.0 onto a multimodal chromatography resin II to capture rHu Ranibizumab and further eliminate impurities with a buffer comprising 20 mM to 50 mM Tris-HCl and 0 mM to 150 mM NaCl having pH ranging from 8.0 to 10.0; and (ii) eluting rHu Ranibizumab in the presence of an elution buffer comprising 20 mM to 50 mM Tris-HCl and 0 mM to 1000 mM NaCl having pH ranging from 8.0 to 10.0.

In one more embodiment, the present invention provides a binding buffer used for binding rHu Ranibizumab to the multimodal chromatography resin II comprising;

(i) 20 mM to 50 mM acetate, and
(ii) 0 mM to 150 mM sodium chloride, with pH in the range of 4.0 to 6.0.

In yet another embodiment, the present invention provides an elution buffer used for eluting rHu Ranibizumab from multimodal chromatography resin II into an elution pool comprising;

(i) 20 mM to 50 mM Tris-HCl, and
(ii) 0 mM to 1000 mM sodium chloride, with pH in the range of 4.0 to 6.0.

The multimodal chromatography resin II is selected from the group consisting of HEA Hypercel™ a high porosity cross-linked cellulose having hexylamine ligands), PPA Hypercel ™a high porosity cross-linked cellulose having phenylpropylamine ligands), and BAKERBOND™ XWP 500 PolyCSX-35 and Capto™ MMC (a cross-linked agarose matrix having —O—CH$_2$—CH(OH)—CH$_2$—O—CH$_2$—CH(OH)—CH$_2$—S—CH$_2$—CH$_2$—CH(COO$^-$)—NH—C(=O)-C$_6$H$_5$ ligands) resin. In bind and elute mode of multimodal chromatography resin II, changing the equilibration buffer pH from 4.0 to 6.5 results in a change in the charge distribution and three dimensional conformation of protein. By combination of ionic interaction, hydrophobic interaction and sample input conductivity, it was observed that in equilibration buffer pH 5.5 and 6.0 mS/cm sample input conductivity, a recovery of 46.57% with product purity of 99.50% was obtained.

TABLE 1

Impact of different pH of equilibration buffer and elution gradient on recovery and purity of rHu Ranibizumab eluted by multimodal chromatography I

| Experiments | Equilibration buffer pH | Elution condition | % recovery | % purity |
|---|---|---|---|---|
| 1 | pH 8.0 | 5.0 CV | 32.67 | 11.65 ± 1.86 |
| 2 | pH 8.0 | 7.5 CV | 44.23 | 11.14 ± 1.01 |
| 3 | pH 8.0 | 10.0 CV | 38.00 | 15.87 ± 1.16 |
| 4 | pH 9.0 | 5.0 CV | 67.06 | 38.25 ± 0.06 |
| 5 | pH 9.0 | 7.5 CV | 60.50 | 37.86 ± 2.17 |
| 6 | pH 9.0 | 10.0 CV | 63.05 | 35.35 ± 1.79 |
| 7 | pH 10.0 | 5.0 CV | 48.95 | 37.97 ± 1.08 |
| 8 | pH 10.0 | 7.5 CV | 48.07 | 37.49 ± 0.67 |
| 9 | pH 10.0 | 10.0 CV | 44.99 | 32.26 ± 2.02 |
| 10 (FIG. 4 and Example 4) | pH 9.0 Sample loading conductivity 6.0 mS/cm | 5.0 CV | 79.19 | 29.69 ± 0.50 |
| 11 (FIG. 5 and Example 5) | pH 9.0 Sample loading conductivity 12.0 mS/cm | 5.0 CV | 76.98 | 33.12 ± 1.02 |

The aforesaid Table 1 lists the varying conditions of equilibration buffer pH and salt concentration which were examined for optimization of conditions along with rHu Ranibizumab recovered from the different sets of experiments.

An increase in pH plays a role in increasing the negative charge on rHu Ranibizumab leading to stronger electrostatic interaction between rHu Ranibizumab and the resin ligand. The salt gradient plays a critical role in selective elution of rHu Ranibizumab. It was observed that elution buffer comprising 20 mM Tris-HCl buffer at pH 9.0 and 5 CV salt elution gradient helped in achieving 38.25% of highly pure product rHu Ranibizumab. At such conditions maximum purity of refolded rHu Ranibizumab was observed, as sample input conductivity and salt concentration in elution have critical impact on hydrophobic interaction of impurities with resin and eluted maximum purified refolded rHu Ranibizumab.

TABLE 2

Impact of different pH of equilibration buffer and sample loading condition on recovery and purity of rHu Ranibizumab eluted in multimodal chromatography II

| Experiments | Equilibration buffer pH | Sample loading conductivity | % Recovery | % Purity |
|---|---|---|---|---|
| 1 | pH 5.5 | 6.0 mS/cm | 46.57 | 99.50 ± 0.08 |
| 2 | pH 5.5 | 7.5 mS/cm | 29.22 | 85.00 ± 0.50 |
| 3 | pH 5.5 | 10.0 mS/cm | 14.10 | 80.00 ± 0.10 |
| 4 | pH 4.5 | 6.0 mS/cm | 42.84 | 60.00 ± 3.02 |
| 5 | pH 6.5 | 6.0 mS/cm | 72.30 | 55.00 ± 1.05 |

Table 2 shows the impact of different pH of equilibration buffer and sample loading condition on recovery and purity of rHu Ranibizumab eluted in multimodal chromatography II. A decrease in pH plays a role in increasing the positive charge on rHu Ranibizumab leading to stronger electrostatic interaction between rHu Ranibizumab and the resin ligand. Hydrophobicity of protein molecules were changed differently in different solution conductivity, which ultimately leads to different binding affinity with resin. It was observed that elution buffer comprising 20 mm acetate buffer at pH 5.5 and 6.0 mS/cm sample loading conductivity helped in achieving 99.50% of highly pure rHu Ranibizumab.

TABLE 3

Process recovery and purity obtained using multimodal chromatographic purification of the present invention

| Sr. No. | Process step | Purity (%) | Yield (%) |
|---|---|---|---|
| 1 | Multimodal chromatography 1 | 38.79 ± 0.65 | 67.56 ± 2.15 |
| 2 | Multimodal chromatography 2 | 99.50 ± 0.08 | 46.57 ± 1.00 |
| 3 | Overall process | 99.50 ± 0.08 | 32.55 ± 2.55 |

TABLE 4

Impurity profile for drug substance produced using multimodal chromatography.

| Sr. No. | Impurity | Ranibizumab produced using claimed purification platform |
|---|---|---|
| 1 | Host cell protein | <100 PPM |
| 2 | Host cell DNA | 41.89 ± 0.54 PPM |
| 3 | Aggregates | 0.49 ± 0.01% |
| 4 | Fragments | <LOQ |

Figure 1:
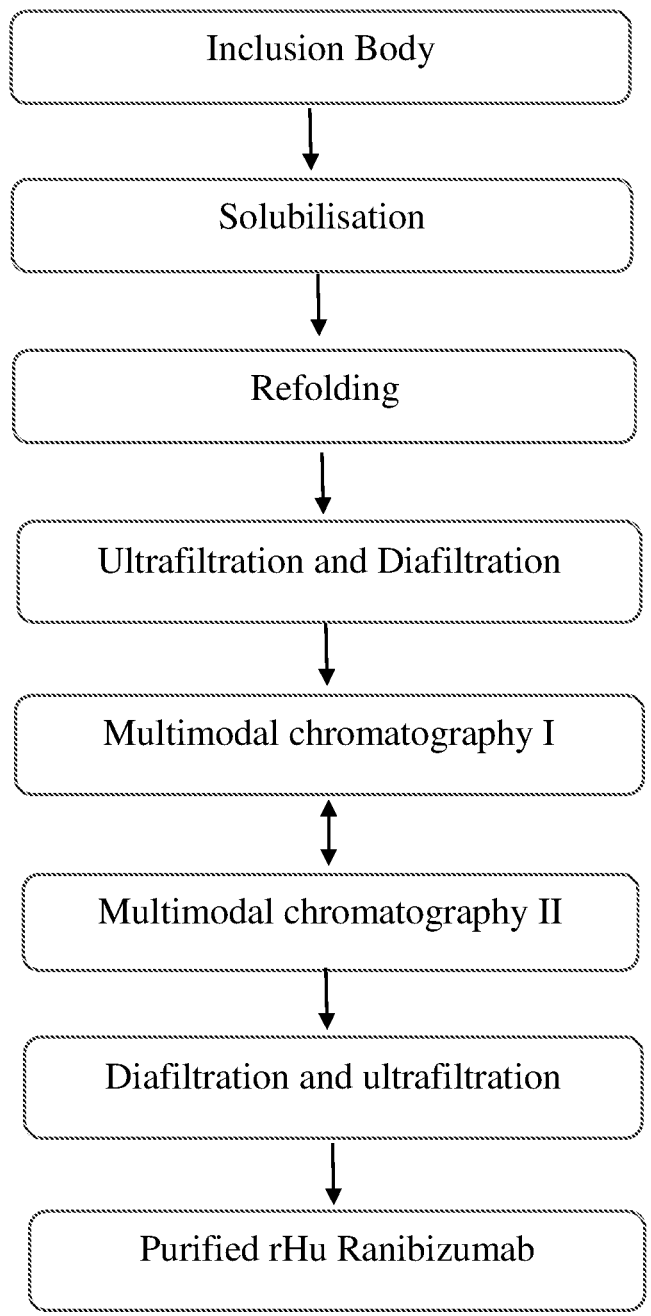
FIG. 1 depicts the process steps for the claimed multimodal chromatographic purification platform.
Figure 2:
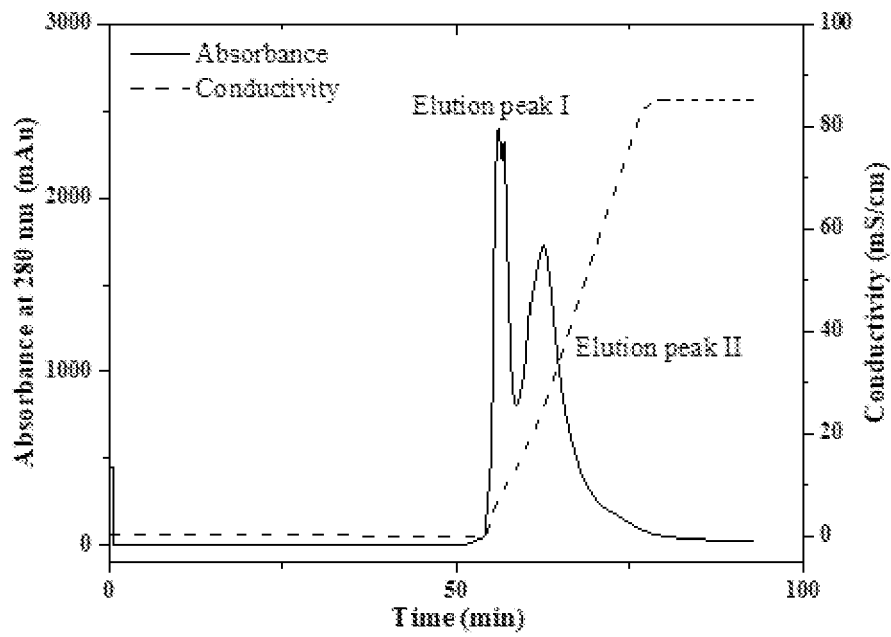
FIG. 2 depicts a chromatogram for multimodal chromatography I, Elution peak I: Purified rHu Ranibizumab, Elution peak II: Product (misfolded and unfolded Ranibizumab) and process related impurities (Host cell proteins and nucleic acids)

Purified Ranibizumab is observed in FIG. 2 in elution peak I indicating 38.79% purity, post elution from the multimodal resin chromatography column I. Elution peak II contains misfolded and unfolded Ranibizumab and process related impurities such as host cell proteins and nucleic acids.

Figure 3:
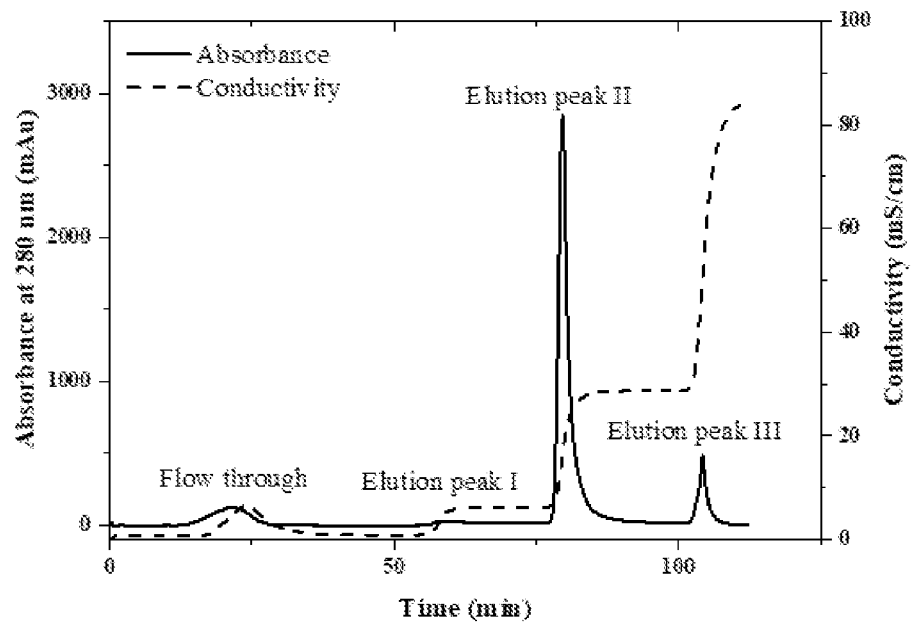
FIG. 3 depicts a chromatogram for multimodal chromatography II, Flow through and Elution peak I: Process related impurities (Host cell proteins and nucleic acids). Elution peak II: Purified rHu Ranibizumab, Elution peak III: Product (misfolded and unfolded Ranibizumab)

Through FIG. 3 it is confirmed that process related impurities including host cell proteins and nucleic acids were observed in flow through and Elution peak I whereas purified Ranibizumab was observed in elution peak II indicating 99.50% purity and product related impurities such as misfolded and unfolded Ranibizumab was observed in Elution peak III.

In another preferred embodiment, the present invention provides a pharmaceutical composition comprising Ranibizumab obtained by the purification process comprising
(i) obtaining rHu Ranibizumab from a recombinant host cell in the form of inclusion bodies;
(ii) solubilizing inclusion bodies using a solubilization buffer to obtain solubilized rHu Ranibizumab;
(iii) refolding the solubilized rHu Ranibizumab using a refolding buffer to obtain refolded rHu Ranibizumab;
(iv) concentrating the refolded rHu Ranibizumab by ultrafiltration to obtain concentrated rHu Ranibizumab;
(v) subjecting the concentrated rHu Ranibizumab to the sequence of the multimodal chromatography purification steps to remove product related impurities, host cell proteins, and host cell nucleic acids and obtain purified rHu Ranibizumab.

In one more preferred embodiment, the present invention provides a recombinant humanized Ranibizumab obtained by the present process.

In one more embodiment, the present invention provides an aqueous composition comprising Ranibizumab obtained from the present process for intra-vitreal administration, wherein the said composition is employed in the treatment and control of age related macular degeneration and associated diseases.

EXAMPLES

The following examples are given by way of illustration only and therefore should not be construed to limit the scope of the present invention in any manner.

Example 1: Bind/Elute Mode Multimodal Chromatography (i) Solubilization of Inclusion Bodies Recombinant Human Ranibizumab expressed in *E. coli* was used in the present invention 0.8 grams of inclusion bodies were initially solubilized in 40 ml solubilization buffer containing 0.1 M Tris pH 9.0, 2 mM EDTA and 6M Guanidine hydrochloride as a denaturant for 30 minutes. Inclusion bodies were solubilized by using a magnetic stirrer for 30 minutes at a temperature of 25° C. After solubilization IB's were centrifuged at 7000 rpm for 10 minutes and filtered using filter paper of pore size 1.0 μm. Dithiothreitol (DTT) was added as the reducing agent such that the concentration of 0.5M DTT in solubilization buffer was 5.0 mM. The solution was kept under stirring condition at 25° C. for 30 minutes for reduction. The soluble and reduced inclusion body solution was kept for oxidation by adding 10.0 mM oxidized glutathione for 3 hr.

(ii) Refolding of Solubilized IB Comprising Ranibizumab

Around 40 mL of solubilized, reduced and oxidized inclusion body solution was added to 960 mL of refolding buffer comprising 0.1 M Tris, 0.6 M Arginine, 5.0% sorbitol and 2 MM EDTA, 0.60 mM cystine and 0.75 mM cysteine, pH 9.0. Refolding process was carried out at 50 rpm, 10±2° C. for 120 hours.

(iii) Ultrafiltration and Diafiltration of Refolded rHu Ranibizumab

Refolded Ranibizumab protein was concentrated by ultrafiltration using 5 kDa Ultrasette™ Lab Tangential Flow Filtration device. Concentration protein was buffer exchanged into 20 mM Tris pH 9.0 using continued diafiltration operation. The buffer exchanged samples were then used as an input for multimodal chromatography.

(iv) Multimodal Chromatography I

Multimodal chromatography I was performed with polyPEI-35 resin. The pH of concentrated refold Ranibizumab was adjusted to 9.0 and was used as feed material. Experiment to capture refolded rHu Ranibizumab was conducted using 20 mM Tris pH 9.0, as an equilibration buffer followed by 3CV salt gradient with 20 mM Tris pH 9.0 containing 1M NaCl. Under such conditions protein was not observed in flow through. Upon RP-HPLC analysis of elution peaks, it was confirmed that purified Ranibizumab was observed in elution peak I (38.79% purity) (FIG. 2). Elution peak II contains the product (misfolded and unfolded Ranibizumab) and process related impurities (Host cell proteins and nucleic acids). In FIG. 2, Elution peak 1 of multimodal chromatography contained purified rHu Ranibizumab which was characterized using SDS PAGE FIG. 9, lane no. 3 at 48 kDa.

(v) Multimodal Chromatography II

Multimodal chromatography II was performed using polyCSX-35 resin. Experiments to capture rHu Ranibizumab were conducted using 10 mM acetate buffer pH 5.50, as equilibration buffer. Elution pool of multimodal chromatography I was used as feed material for multimodal chromatography II. The pH of feed material was adjusted to pH 5.50 with glacial acetic acid. Elution was performed using salt based step gradient 10 mM acetate buffer pH 5.50 containing 1M NaCl. After selective removal of process related impurities in 10% of gradient, pure Ranibizumab was eluted using 45% of elution step gradient. Upon RP-HPLC analysis of these peaks it was confirmed that process related impurities (Host cell proteins and nucleic acids) were observed in flow through and Elution peak I whereas purified Ranibizumab was observed in elution peak II (99.50% purity) and product related impurities (misfolded and unfolded Ranibizumab) was observed in Elution peak III (FIG. 3). Quality of the product was verified using SDS PAGE analysis and was found in good agreement with that of standard Ranibizumab. (Lane no. 1 at 48 kDa of FIG. 7)

Example 2: Bind-Elute Multimodal Chromatography I and II

Refolding rHu Ranibizumab and Pre-Treatment Thereof (i) Solubilization of Inclusion Bodies 0.4 grams IB comprises recombinant human Ranibizumab expressed in *E. coli* were dissolved in 20 mL solubilization buffer containing 0.1 M Tris pH 9.0, 2.0 mM EDTA and 6.0 M Guanidine hydrochloride as a denaturant for 30 min. Further processing was performed as per the process of Example 1(i).

(ii) Refolding of Solubilized Inclusion Bodies

Refolding was performed in accordance with the process disclosed in Example 1(ii).

(iii) Ultrafiltration and Diafiltration of Refolded rHu Ranibizumab

Ultrafiltration and diafiltration of refolded rHu Ranibizumab was performed as per the process disclosed in Example 1 (iii).

(iv) Multimodal Chromatography I

Multimodal chromatography I was performed with polyPEI-35 resin. The pH of concentrated refold Ranibizumab was adjusted to 10.0 and was used as feed material. Experiment to capture refolded rHu Ranibizumab was conducted using 20.0 mM Tris pH 10.0, as an equilibration buffer followed by 5.0 CV salt gradient with 20.0 mM Tris pH 10.0 containing 1.0 M NaCl. No protein was observed in flow through. Upon RP-HPLC analysis of elution peaks, it was confirmed that purified Ranibizumab was observed in elution peak I (37.97% purity). Elution peak II contains the product (misfolded and unfolded Ranibizumab) and process related impurities (Host cell proteins and nucleic acids).

(v) Multimodal Chromatography II

Multimodal chromatography II was performed using polyCSX-35 resin. Experiments to capture rHu Ranibizumab was conducted using 10.0 mM acetate buffer pH 5.5, as an equilibration buffer. Elution pool of multimodal chromatography I was used as a feed material for multimodal chromatography II. The pH of feed material was adjusted to pH 5.5 with glacial acetic acid. Elution was performed using salt based step gradient 10 mM acetate buffer pH 5.5 containing 1.0 M NaCl. After selective removal of process related impurities in 10% of gradient, pure Ranibizumab was eluted using 45% of elution step gradient. Upon RP-HPLC analysis of these peaks, it was confirmed that process related impurities (Host cell proteins and nucleic acids) were observed in flow through and Elution peak I whereas purified Ranibizumab was observed in elution peak II (99.50% purity) (FIG. 3) and product related impurities (misfolded and unfolded Ranibizumab) was observed in Elution peak III.

Example 3: Flow Through Mode Multimodal Chromatography I and Bind and Elute Mode Multimodal Chromatography II Refolding of rHu Ranibizumab and Pre-Treatment:
(i) Solubilization of the Inclusion Bodies Recombinant Human Ranibizumab expressed in *E. coli* was used in this investigation. 0.267 grams of inclusion bodies (IB's) were dissolved in 13.3 mL solubilization buffer. Further processing is as per the process performed in Example 1 (i).
(ii) Refolding of Solubilized Inclusion Bodies 13.3 mL of solubilized, reduced and oxidized inclusion body was added into 986.7 mL of refolding buffer and the process was performed in accordance with Example 1(ii).
(iii) Ultrafiltration and Diafiltration of Refolded rHu Ranibizumab Refolded Ranibizumab protein was concentrated by ultrafiltration using 5 kDa Ultrasette™ Lab Tangential Flow Filtration device. Concentration protein was buffer exchanged into 20 mM Tris pH 8.0 using continued diafiltration operation. The buffer exchanged samples were then used as an input for multimodal chromatography.
(iv) Multimodal Chromatography I Multimodal chromatography I was performed with poly-PEI-35 resin. The pH of concentrated refolded Ranibizumab was adjusted to 8.0 and was used as feed material. Experiment to capture refolded rHu Ranibizumab was conducted using 20.0 mM Tris pH 8.0, as equilibration buffer followed by 5.0 CV salt gradient with 20.0 mM Tris pH 8.0 containing 1.0 M NaCl. Under such conditions refolded rHu Ranibizumab was observed in flow through. Upon RP-HPLC analysis of flow through, it was confirmed that purified Ranibizumab was observed in flow through (31.24% purity). Elution peak I and Elution peak II contains the product (misfolded and unfolded Ranibizumab) and process related impurities (Host cell proteins and nucleic acids), respectively.

(v) Multimodal Chromatography II

Multimodal chromatography II was performed using polyCSX-35 resin. Experiments to capture rHu Ranibizumab was conducted using 10.0 mM acetate buffer pH 5.5 as equilibration buffer. Flow through of multimodal chromatography I was used as feed material for multimodal chromatography II. The pH of feed material was adjusted to pH 5.5 with glacial acetic acid. Elution was performed using salt based step gradient 10.0 mM acetate buffer pH 5.5 containing 1.0 M NaCl. After selective removal of process related impurities in 10% of gradient, pure Ranibizumab was eluted using 45% of elution step gradient. Upon RP-HPLC analysis of these peaks it was confirmed that process related impurities (Host cell proteins and nucleic acids) were observed in flow through and elution peak I whereas purified Ranibizumab was observed in elution peak II (99.50% purity) and product related impurities (misfolded and unfolded Ranibizumab) was observed in Elution peak III.

Example 4: Flow Through Mode Multimodal Chromatography I and Bind and Elute Mode Multimodal Chromatography II (i) Solubilization of the Inclusion Bodies
Solubilization was performed as per the process of Example 2(i).
(ii) Refolding of the Solubilized Inclusion Bodies
Refolding was performed as per the process of Example 2(ii).
(iii) Ultrafiltration of Refolded rHu Ranibizumab
Refolded Ranibizumab protein was concentrated by ultrafiltration using 5 kDa Ultrasette™ Lab Tangential Flow Filtration devise. Concentrated protein samples were then used as an input for the multimodal chromatography I.
(iv) Multimodal Chromatography I Multimodal chromatography I was performed in flow through mode with polyPEI-35 resin. The pH of the concentrated refolded Ranibizumab was adjusted to 9.0, conductivity was adjusted to 6.0 mS/cm and was used as a feed material. Experiment to capture refolded rHu Ranibizumab in flow through was conducted using 20.0 mM Tris pH 9.0, as an equilibration buffer followed by 5.0 CV salt gradient with 20.0 mM Tris pH 9.0 containing 1.0 M NaCl to remove impurities. Under this experimental condition refolded rHu Ranibizumab was observed in flow through. Upon RP-HPLC analysis of the flow through, it was conformed that purified Ranibizumab was observed in flow through (29.69% purity. Elution Peak I and Elution peak II contains the product (misfolded and unfolded Ranibizumab) and process related impurities (Host cell proteins and nucleic acids). FIG. 4 shows the chromatogram for the multimodal chromatography I carried out for the purification of rHu Ranibizumab.
(v) Multimodal Chromatography II Multimodal chromatography II was performed using polyCSX-35 resin. Experiments to capture rHu Ranibizumab was conducted using 10.0 mM acetate buffer pH 5.50, as an equilibration buffer. Elution pool of multimodal chromatography I was used as a feed material for multimodal chromatography II. The pH of feed material was adjusted to pH 5.5 with glacial acetic acid. Elution was performed using salt based step gradient 10.0 mM Acetate buffer pH 5.5 containing 1M NaCl. After selective removal of process related impurities in 10.0% of the gradient, pure Ranibizumab was eluted using 45.0% of elution step gradient. Upon RP-HPLC analysis of these peaks it was confirmed that process related impurities (Host cell proteins and nucleic acids) were observed in flow through and Elution peak I whereas purified Ranibizumab was observed in elution peak II (99.50% purity) and product related impurities (misfolded and unfolded Ranibizumab) was observed in Elution peak III.

Example 5: Flow Through Mode Multimodal Chromatography I and Bind and Elute Mode Multimodal Chromatography II (i) Solubilization of Inclusion Bodies
Solubilization of inclusion bodies was performed as per the process of Example 2(i).
(ii) Refolding of the Solubilized Inclusion Bodies
Refolding was performed as per the process of Example 2(ii).
(iii) Ultrafiltration and Diafiltration of Refolded rHu Ranibizumab
Ultrafiltration of refolded rHu Ranibizumab was performed as per process in Example 4 (iii).
(iv) Multimodal Chromatography I
Multimodal chromatography I was performed in flow through mode with polyPEI-35 resin. The pH of the concentrated refolded Ranibizumab was adjusted to 9.0, conductivity was adjusted to 12.0 mS/cm and was used as a feed material. Experiment to capture refolded rHu Ranibizumab in flow through was conducted using 20.0 mM Tris pH 9.0, as an equilibration buffer followed by 5.0 CV salt gradient with 20.0 mM Tris pH 9.0 containing 1.0 M NaCl to remove impurities. Under this experimental condition refolded rHu Ranibizumab was observed in flow through. Upon RP-HPLC analysis of the flow through, it was conformed that purified Ranibizumab was observed in flow through (33.12% purity) (FIG. 5). Elution Peak I and Elution peak II contains the product (misfolded and unfolded Ranibizumab) and process related impurities (Host cell proteins and nucleic acids). FIG. 5 shows the chromatogram for the multimodal chromatography I carried out for the purification of rHu Ranibizumab.
(v) Multimodal Chromatography II
Multimodal chromatography II was performed using polyCSX-35 resin. Experiments to capture the rHu Ranibizumab was conducted using 10.0 mM Acetate buffer pH 5.5, as an equilibration buffer. Elution pool of multimodal chromatography I was used as a feed material for the multimodal chromatography II. The pH of the feed material was adjusted to pH 5.5 with glacial acetic acid. Elution was performed using salt based step gradient 10 mM acetate buffer pH 5.5 containing 1.0 M NaCl. After selective removal of the process related impurities in 10.0% of the gradient pure Ranibizumab was eluted using 45.0% of the elution step gradient. Upon RP-HPLC analysis of these peaks it was confirmed that process related impurities (Host cell proteins and nucleic acids) were observed in flow through and Elution peak I whereas purified Ranibizumab was observed in elution peak II (99.50% purity) and product related impurities (misfolded and unfolded Ranibizumab) was observed in Elution peak III.

Example 6: Bind and Elute Mode Multimodal Chromatography II Followed by Bind and Elute Mode Multimodal Chromatography I (i) Solubilization of Inclusion Bodies
Solubilization process was performed as per the process of Example 1(i).
(ii) Refolding of the Solubilized Inclusion Bodies
Refolding process was performed as per the process of Example 1(ii).
(iii) Ultrafiltration and Diafiltration of Refolded rHu Ranibizumab
Refolded Ranibizumab protein was concentrated by ultrafiltration using 5 kDa Ultrasette™ Lab Tangential Flow Filtration devise. The pH of concentrated protein sample was then adjusted to pH 5.5 with glacial acetic acid. Conductivity of concentrated refolded protein sample was adjusted to 10.0 mS/cm. Host cell protein was precipitated at pH 5.5. Precipitated host cell protein was removed by centrifugation at 8000 rpm for 15 min and supernatant of refolded protein was then used as an input for the multimodal chromatography II.
(iv) Multimodal Chromatography II
Multimodal chromatography II was performed using polyCSX-35 resin. Experiments to capture rHu Ranibizumab were conducted using 10.0 mM Acetate buffer pH 5.50, as equilibration buffer. Elution was performed using salt based step gradient 10.0 mM acetate buffer pH 5.5 containing 1.0 M NaCl. After selective removal of process related impurities in 10% of gradient pure Ranibizumab was eluted using 45% of elution step gradient. Upon RP-HPLC analysis of these peaks it was confirmed that process related impurities (Host cell proteins and nucleic acids) were observed in flow through and Elution peak I whereas purified Ranibizumab was observed in elution peak II and product related impurities (misfolded and unfolded Ranibizumab) was observed in Elution peak III.
(v) Multimodal Chromatography I
Multimodal chromatography I was performed in flow through mode with polyPEI-35 resin. The pH of the output of multimodal chromatography II was adjusted pH 9.0. Experiment to capture refolded rHu Ranibizumab in flow through was conducted using 20.0 mM Tris pH 9.0, as an equilibration buffer followed by 5 CV salt gradient with 20.0 mM Tris pH 9.0 containing 1.0 M NaCl to remove impurities. Under this experimental condition refolded rHu Ranibizumab was observed in flow through. Upon RP-HPLC analysis of the flow through, it was conformed that purified Ranibizumab was observed in flow through. Elution Peak I and Elution peak II contains the product (misfolded and unfolded Ranibizumab) and process related impurities (Host cell proteins and nucleic acids).

Example 7: Bind—Elute Mode Multimodal Chromatography I and II

In-Vivo Soluble Expression of rHu Ranibizumab and Pre-Treatment:
(i) Expression of Soluble rHu Ranibizumab in Mutated *E. coli*
*E. coli* cells comprising expressed recombinant human Ranibizumab was harvested and resuspended in lysis buffer (20.0 mM Tris, 0.1 mM EDTA, pH 9.0) at a cell pellet: buffer ratio of 1:10 (w/v). Cell lysis was done using high-pressure homogenizer at 15000 bar pressure for 20 min. The cell lysate was centrifuged at 10000 rpm for 30 minutes at 4° C. to obtain supernatant of cell lysate.

(ii) Ultrafiltration and Diafiltration of Refolded rHu Ranibizumab

Soluble rHu Ranibizumab was buffer exchanged into 20.0 mM Tris pH 9.0 using continuous diafiltration operation. The buffer exchanged samples were used as an input for the multimodal chromatography.

(iii) Multimodal Chromatography I

Multimodal chromatography I was performed with poly-PEI-35 resin. The pH of the concentrated soluble rHu Ranibizumab was adjusted to 9.0 and was used as a feed material. Experiment to capture soluble rHu Ranibizumab was conducted using 20.0 mM Tris pH 9.0, as an equilibration buffer followed by 5.0 CV salt gradient with 20.0 mM Tris pH 9.0 containing 1.0 M NaCl. Under this experimental condition no protein was observed in flow through. Upon RP-HPLC analysis of the elution peaks, it was conformed that purified Ranibizumab was observed in elution peak I (38.79% purity). Elution peak II contains the product (misfolded and unfolded Ranibizumab) and process related impurities (Host cell proteins and nucleic acids).

(iv) Multimodal Chromatography II

Multimodal chromatography II was performed using polyCSX-35 resin. Experiments to capture the rHu Ranibizumab was conducted using 10.0 mM Acetate buffer pH 5.50, as an equilibration buffer. Elution pool of multimodal chromatography I was used as a feed material for the multimodal chromatography II. The pH of the feed material was adjusted to pH 5.50 with glacial acetic acid. Elution was performed using salt based step gradient 10.0 mM Acetate buffer pH 5.50 containing 1.0 M NaCl. After selective removal of the process related impurities in 10.0% of the salt gradient, pure rHu Ranibizumab was eluted using 45.0% of the elution step gradient. Upon RP-HPLC analysis of these peaks it was confirmed that process related impurities (Host cell proteins and nucleic acids) were observed in flow through and Elution peak I whereas purified Ranibizumab was observed in elution peak II (FIG. 3) and product related impurities (misfolded and unfolded Ranibizumab) was observed in Elution peak III. Quality of the product was verified using SDS PAGE analysis and was found in good agreement with that of standard Ranibizumab. (Lane no. 3 at 48 kDa of FIG. 10)

Example 8: Bind and Elute Mode Multimodal Chromatography I and II (i) Solubilization of the Inclusion Bodies Solubilization was performed in accordance with Example 1(i).

(ii) Refolding of the Solubilized Inclusion Bodies

Refolding was performed in accordance with Example 1(ii).

(iii) Ultrafiltration and Diafiltration of Refolded rHu Ranibizumab

Filtration was performed in accordance with Example 1(iii).

(iv) Multimodal Chromatography I

Multimodal chromatography I was performed with Capto adhere resin. The pH of the concentrated refolded Ranibizumab was adjusted to 9.0 and was used as a feed material. Experiment to capture refolded rHu Ranibizumab was conducted using 20.0 mM Tris pH 9.0, as an equilibration buffer followed by 5.0 CV salt gradient with 20.0 mM Tris pH 9.0 containing 1.0 M NaCl. Under this experimental condition no protein was observed in flow through. Upon RP-HPLC analysis of the elution peaks, it was conformed that purified Ranibizumab was observed in elution peak I (38.79% purity). Elution peak II contains the product (misfolded and unfolded Ranibizumab) and process related impurities (Host cell proteins and nucleic acids).

(v) Multimodal Chromatography II

Multimodal chromatography II was performed using Capto MMC resin. Experiments to capture the rHu Ranibizumab was conducted using 10.0 mM Acetate buffer pH 5.50, as an equilibration buffer. Elution pool of multimodal chromatography I was used as a feed material for the multimodal chromatography II. The pH of the feed material was adjusted to pH 5.50 with glacial acetic acid. Elution was performed using salt based step gradient 10 mM Acetate buffer pH 5.50 containing 1.0 M NaCl. After selective removal of the process related impurities in 10.0% of the salt gradient, pure rHu Ranibizumab was eluted using 45.0% of the elution step gradient. Upon RP-HPLC analysis of these peaks. It was confirmed that process related impurities (Host cell proteins and nucleic acids) were observed in flow through and Elution peak I whereas purified Ranibizumab was observed in elution peak II and product related impurities (misfolded and unfolded Ranibizumab) was observed in Elution peak III.

Example 9: Analytical Characterization of Recombinant Ranibizumab (i) Absorbance Measurement at A280 for Ranibizumab Samples Total protein in refold and chromatography outputs was determined using UV absorbance measurement at 280 nm. All collected fraction were read at 280 nm using Nanodrop 2000 and UV-1800 Shimadzu UV Visible spectrophotometer.

(ii) Bradford's Assay for Total Protein Estimation for Ranibizumab:

An orthogonal technique used for the total protein estimation was the Bradford's assay at 595 nm using Nanodrop 2000. After adding 5 µl of the sample into 250 µl of Bradford reagent, mixing was performed on the shaker for 30 seconds. After mixing, the sample was incubated in presence of the dye for 25 minutes and absorbance was measured at 595 nm.

(iii) Reverse Phase HPLC Analysis for Quantitation of Ranibizumab

Concentration of rHu Ranibizumab in various chromatography outputs was determined using 4.6 mm×150 mm Aeris™ 3.6 um WIDEPORE XB C18 column on Agilent 1260 HPLC system (FIG. 11). The mobile phase consisted of 0.1% (v/v) TFA in water (solvent A) and 0.1% (v/v) TFA, 70% (v/v) of acetonitrile, 20% (v/v) Isopropanol in water (solvent B). Flow rate was maintained at 1 ml/min using a linear gradient of A to B at a wavelength of 214 nm. For the purified refolded Ranibizumab FIG. 11(b) obtained by the process of the preset invention a peak (retention time: 28.1 minutes) is similar to the peak obtained in FIG. 11(a) for the innovator Ranibizumab.

(iv) SDS PAGE Analysis of Ranibizumab Samples

SDS PAGE analysis for identification of process and product related impurities associated with Ranibizumab was carried out using 12% (Thickness 1 mm) of resolving gel under non reducing (FIG. 7) and reducing condition (FIG. 8) at stacking gel constant voltage 120V and resolving gel constant voltage 100V conditions. Each sample was boiled for 10 min in the starting buffer before being loaded into the gel. 0.05% (w/v) Coomassie brilliant blue G-250 in 4:1:5 (Water: Glacial Acetic acid: Methanol) was used to detect proteins after electrophoretic separation on polyacrylamide gels. Analysis of gel in FIG. 7 indicates presence of a 48 kDa protein band in lane 1 for purified refolded protein, thereby confirming presence of rHu Ranibizumab. Reducing gel results in FIG. 8 shows presence of light and heavy chain of Ranibizumab. FIGS. 7 and 8 shows biosimilarity with the innovator molecule.

(v) ELISA Analysis for Quantification of an In-Vitro Bioactivity of Ranibizumab Samples Immuno enzymatic assay (Lucentis/Ranibizumab, Anti-VEGF ELISA Kit for human from Alpha diagnostic international, USA). Samples containing purified refolded Ranibizumab was reacted with VEGF antigen coated on the plate. Bounded Ranibizumab detected by horseradish peroxidase (HRP) enzyme labeled anti human IgG. The immunological reactions result in the formation of a sandwich complex of solid phase VEGF bounded antibody-Ranibizumab-enzyme labeled antibody. The microtiter strips are washed to remove any unbound reactants. The substrate, tetramethylbenzidine (TMB) is then reacted. The amount of hydrolyzed substrate is read on a microtiter plate reader at 450 nm and is directly proportional to the concentration of Ranibizumab present.

(vi) ELISA Analysis for Host Cell Protein (HCP) Quantitation of Ranibizumab

Host cell protein contamination in anion exchange chromatography flow through was analyzed using a two-site immuno enzymatic assay (Cygnus *E. coli*. HCP analysis kit F 410). Samples containing *E. coli* HCPs were reacted with a horseradish peroxidase (HRP) enzyme labeled anti-*E. coli* antibody simultaneously in microtiter strips coated with an affinity purified capture anti-*E. coli* antibody. The immunological reactions result in formation of a sandwich complex of solid phase antibody-HCP-enzyme labeled antibody. The microtiter strips are washed to remove any unbound reactants. The substrate, tetramethylbenzidine (TMB) is then reacted. The amount of hydrolyzed substrate is read on a microtiter plate reader at 450 nm and is directly proportional to the concentration of *E. coli* HCPs present.

(vii) SE HPLC Analysis of Ranibizumab Samples:

Aggregate content in the various process outputs was determined using SEC-HPLC analysis (FIG. 12) performed using Yarra™3 um SEC-2000 (300×7.8 mm ID) column. The mobile phase consists of 20 mM acetate buffer with 50 mM sodium chloride buffer at pH 5.50. Analysis was done in isocratic mode with 0.5 ml/min flow rate at 25° C. Protein detection was done using photo diode array detector at 280 nm.

(viii) Double Stranded DNA Estimation:

Presence of DNA in the output samples was estimated using Quant-iT™ picogreen assay (Invitrogen BioServices India Private Limited, India). Standard curve was prepared using double stranded lambda DNA. 0.5 ml of the process output sample was added to the 0.5 ml of diluted Quant-iT™ dsDNA BR reagent and the reaction mixture was incubated for 5 minutes. After five-minute fluorescence was measured using fluorescence spectrophotometer (excitation wavelength 480 nm and emission wavelength 520 nm).

(viii) Intact Mass Analysis of Purified rHu Ranibizumab by Matrix-Assisted Laser Desorption/Ionization (MALDI-TOF)

Standard and purified rHu Ranibizumab with sinapinic acid matrix was mixed in 1:1 ratio to perform MALDI-TOF analysis. Matrix sinapinic acid (10 mg/ml) was prepared in 30% v/v acetonitrile, 0.1% v/v TFA in high purity water. 1 µl of homogenize mixture of sample and matrix was deposited on clean 384 well MALDI plate. Plate was inserted into AB SCIEX TOF/TOF™ 5800 instrument. Instrument was used in positive ion mode. Nitrogen laser at 337 nm radiation was kept as an ionization source. Laser intensity in between 4000 to 5000 was used for the analysis of samples. Result analysis was performed (FIG. 13) using Protein-Pilot™ software. Analysis of FIG. 13 shows comparability between intact mass of purified rHu Ranibizumab obtained using developed purification platform and innovator Ranibizumab molecule.

(ix) Peptide Fingerprinting by LC-MS.

Coomassie stained protein band from SDS-PAGE analysis was excised and chopped into small pieces with a scalpel on a glass plate. Gel pieces were washed with 100 mM $NH_4HCO_3$ and detained by adding 200 µl 50% acetonitrile and 50% 50 mM $NH_4HCO_3$, vortex and incubate it for 10 minutes. Liquid was removed and again washed with 100% acetonitrile to dehydrate gel pieces. Acetonitrile was removed and air-dried in fume hood for 10 minutes. Gel pieces were covered with 50 µl, 10 mM DTT in 100 mM $NH_4HCO_3$ for 45-60 minutes at 56° C. for reduction and alkylation. DTT solution was removed and 50 µl of 55 mM iodoacetamide in 100 mM $NH_4HCO_3$ was added and incubated for 45 min in dark place at room temperature. Iodoacetamide was removed. Gel pieces were washed with 100 µl of 100 mM $NH_4HCO_3$ for 5 minutes with vortexing, then twice with 50% acetonitrile+50% 50 mM $NH_4HCO_3$ for 5 minutes with vortexing. Gel was dehydrated with 100 µl acetonitrile as above. Remaining liquid was removed and dried it by using speedvac. 20 µl trypsin (12.5 ng/µl) solution was added for trypsin digestion to just cover the gel pieces. The gel pieces were rehydrated at 4° C. for 30 minute in buffer containing 50 mM $NH_4HCO_3$ and trypsin. Gel pieces were put for overnight digestion at 37° C. The digested supernatant was transferred into a clean 1.5 mL Eppendorf tube for peptide extraction. 30 µL of 50% acetonitrile and 2% formic acid was added into gel pieces, incubated for 20 min. Peptide solution was sonicated for 5 minute in a water bath with no heat. Supernatant was removed and combined with initial digest solution. Peptide solution was then dried by speedvac concentrator. Peptide sample was reconstituted into 3.0% v/v acetonitrile, 0.1% v/v formic acid in highly pure water. 4 µL sample (2.5 µg) was loaded into Agilent ZORBAX RRHD 300SB-C18, 0.3×100 mm, 3 µm column and analyzed by Q Exactive Orbitrap LC-MS/MS System.

Advantages of the Present Invention

Almost two-fold improvement in productivity over existing manufacturing process was obtained by integrating the multimodal chromatographic purification steps for rHu Ranibizumab downstream processing.

Orthogonal analytical tests established an analytical comparability between the purified drug substance obtained using the present invention and the innovator Ranibizumab molecule.

The developed purification platform is applicable to both in-vitro refolded and soluble expressed antibody fragments

We claim:

1. A process for purification of recombinant humanized (rHu) Ranibizumab from a recombinant host cell expressed as inclusion bodies, said process comprising;
   (a) solubilizing inclusion bodies containing light and heavy chains of rHu Ranibizumab from a recombinant host cell to obtain a solubilized rHu Ranibizumab;
   (b) refolding the solubilized rHu Ranibizumab of step (a) to obtain a refolded rHu Ranibizumab;

(c) concentrating the refolded rHu Ranibizumab of step (b) by ultra-filtration to obtain a concentrated and refolded rHu Ranibizumab;

(d) subjecting the concentrated and refolded rHu Ranibizumab of step (c) to a first multimodal chromatography process, said first multimodal chromatography process comprising:

(i) binding concentrated and refolded rHu Ranibizumab of step (c) having pH ranging from 4.0 to 10.0 onto a first multimodal chromatography resin to capture the rHu Ranibizumab and eliminate impurities, with a buffer comprising 20 mM to 50 mM Tris HCl and 0 mM to 150 mM NaCl, or 20 mM to 50 mM acetate and 0 mM to 150 mM NaCl, with pH ranging from 4.0 to 10.0, (ii) eluting rHu Ranibizumab in the presence of an elution buffer comprising 20 mM to 50 mM Tris HCl and 0 mM to 1000 mM sodium chloride, or 20 mM to 50 mM acetate and 0 mM to 1000 mM sodium chloride, with pH ranging from 4.0 to 10.0 into an elution pool;

wherein the rHu Ranibizumab purified in step (d) has less than 5% of unfolded or misfolded forms of rHu Ranibizumab and less than 2% of aggregated form of rHu Ranibizumab;

(e) subjecting the rHu Ranibizumab of step (ii) of step (d) to a second multimodal chromatography process, said second multimodal chromatography process comprising:

(iii) feeding rHu Ranibizumab from the elution pool of step (ii) of step (d) having pH ranging from 4.5 to 6.5 onto a second multimodal chromatography resin to capture rHu Ranibizumab with a buffer comprising 20 mM to 50 mM acetate and 0 mM to 150 mM NaCl having pH ranging from 4.0 to 6.5; and (iv) eluting rHu Ranibizumab with an elution buffer comprising 20 mM to 50 mM acetate and 0 mM to 1000 mM NaCl having pH ranging from 4.0 to 6.5;

wherein the rHu Ranibizumab purified in step (e) has less than 0.1% of unfolded or misfolded forms of rHu Ranibizumab and less than 0.3% of aggregated form of rHu Ranibizumab.

2. The process as claimed in claim 1, wherein:
pH conditions for the first multimodal chromatography process range from 8.0 to 10. 0.

3. The process as claimed in claim 1, wherein
(i) applying input conductivity of 12 mS/cm during step (c) at a pH of 9 results in a rHu Ranibizumab purity of 38.25%, and
(ii) applying input conductivity 6 mS/cm-during step (e) at a pH of 5.5 results in a rHu Ranibizumab purity of 99.50%.

4. The process as claimed in claim 1, wherein the rHu Ranibizumab purified in step (e) has a percent purity of 99.50±0.08%.

5. The process as claimed in claim 1, wherein the % yield of rHu Ranibizumab in the process is 32.55±2.55%.

6. A process for purification of recombinant humanized (rHu) Ranibizumab from a recombinant host cell expressed as inclusion bodies, said process comprising;

(a) solubilizing inclusion bodies containing light and heavy chains of rHu Ranibizumab from a recombinant host cell to obtain a solubilized rHu Ranibizumab;

(b) refolding the solubilized rHu Ranibizumab of step (a) to obtain a refolded rHu Ranibizumab;

(c) concentrating the refolded rHu Ranibizumab of step (b) by ultra-filtration to obtain a concentrated and refolded rHu Ranibizumab;

(d) subjecting the concentrated and refolded rHu Ranibizumab of step (c) to a first multimodal chromatography process, said first multimodal chromatography process comprising:

(i) feeding concentrated and refolded rHu Ranibizumab of step (c) having pH ranging from 4.5 to 6.5 onto a first multimodal chromatography resin to capture rHu Ranibizumab with a buffer comprising 20 mM to 50 mM acetate and 0 mM to 150 mM NaCl having pH ranging from 4.0 to 6.5; and (ii) eluting rHu Ranibizumab with an elution buffer comprising 20 mM to 50 mM acetate and 0 mM to 1000 mM NaCl having pH ranging from 4.0 to 6.5; and (e) subjecting the rHu Ranibizumab of step (ii) to a second multimodal chromatography process, said second multimodal chromatography process comprising:

(iii) binding the rHu Ranibizumab of step (ii) of step (d) having pH ranging from 4.0 to 10.0 onto a second multimodal chromatography resin to capture the rHu Ranibizumab and eliminate impurities, with a buffer comprising 20 mM to 50 mM Tris HCl and 0 mM to 150 mM NaCl, or 20 mM to 50 mM acetate and 0 mM to 150 mM NaCl, with pH ranging from 4.0 to 10.0, (iv) eluting rHu Ranibizumab in the presence of an elution buffer comprising 20 mM to 50 mM Tris HCl and 0 mM to 1000 mM sodium chloride, or 20 mM to 50 mM acetate and 0 mM to 1000 mM sodium chloride, with pH ranging from 4.0 to 10.0 into an elution pool.

7. The process as claimed in claim 6, wherein pH conditions for the second multimodal chromatography process range from 8.0 to 10.0.

* * * * *